US005716372A

United States Patent [19]

Yoo

[11] Patent Number: 5,716,372

[45] Date of Patent: Feb. 10, 1998

[54] SET OF NEEDLES FOR HANDS

[76] Inventor: Tae Woo Yoo, 807, 1-Dong, Hanyang, Apt. 32-5, Banpo-dong, Seocho-ku, Seoul, Rep. of Korea

[21] Appl. No.: 786,191

[22] Filed: Jan. 17, 1997

Related U.S. Application Data

[63] Continuation of Ser. No. 389,188, Feb. 15, 1995.

[30] Foreign Application Priority Data

Nov. 21, 1994 [KR] Rep. of Korea ........................ 94-30744

[51] Int. Cl.[6] ........................ A61B 17/34

[52] U.S. Cl. ........................ 606/189; 128/907

[58] Field of Search ........................ 606/189; 128/907; 206/380, 353

[56] References Cited

U.S. PATENT DOCUMENTS

| | | | |
|---|---|---|---|
| 111,051 | 1/1871 | Fowler | 206/380 |
| 3,331,499 | 7/1967 | Jost | 206/380 |
| 3,957,053 | 5/1976 | Woo | 606/189 |
| 4,573,575 | 3/1986 | Bergrath et al. | 206/380 |
| 5,067,611 | 11/1991 | Hagmann et al. | 206/383 |
| 5,129,914 | 7/1992 | Choi | 606/189 |
| 5,316,142 | 5/1994 | Jain | 206/380 |

FOREIGN PATENT DOCUMENTS

| | | | |
|---|---|---|---|
| 2600-530-A | 12/1987 | France | 606/189 |
| 3522-855-A | 3/1986 | Germany | 606/189 |
| 1477-415-A | 5/1989 | U.S.S.R. | 606/189 |

*Primary Examiner*—Michael Buiz
*Assistant Examiner*—Patrick W. Rasche
*Attorney, Agent, or Firm*—Richard M. Goldberg

[57] ABSTRACT

A set of needles for hands includes a plurality of needles which are arranged and pressured between upper and lower synthetic resin films at regular intervals, in which cutting lines are formed between the needles for hands, and grooves and slant portions are formed at the upper and lower parts of the cutting lines, respectively. Thus, where necessary, each needle for hands can be used by cutting from adjacent ones according to the cutting lines from the grooves. Accordingly, because a set of needles for hands is produced at once, this invention has the advantages of reduction of the manufacturing process, an inexpensive supply and a reduction of the burden of household economy.

2 Claims, 4 Drawing Sheets

SET OF NEEDLES FOR HANDS

This application is a continuation of application Ser. No. 08/389,188 filed Feb. 15, 1995.

BACKGROUND OF THE INVENTION

1. Field of the Invention

The present invention relates to a set of needles for hands and is an improvement over Korean Utility Model Patent Application No. 94-16851. More particularly, this invention relates to a set of needles for hands which are obtained by the process in which, upon inserting a plurality of needles between two synthetic resin rims, it is pressured, and then, cutting lines and grooves are shaped, and can be used to divide adjacent ones according to a cutting line in case of need, so that it is convenient for use, easy for mass production and economical.

2. Description of the Prior Art

Conventional needles are so small that acupuncture cannot directly be applied by hand. Thus when the acupuncture is applied, an inserter must be used. However, when there are many needle points to be applied with acupuncture, it is inconvenient for use. Furthermore, owing to the constant force of gravity of the plunger, there may be differences in the inserting depth according to the individual characteristic of the skin or the difference of the skin of the front and back of the hand.

Also in said Korean Utility Model Patent Application No. 94-16851, there is disclosed a needle assembly for performing acupuncture treatment which can directly apply acupuncture with the pressed portion and/or the tubular shaft portion held by the hand. However, there is a difficult problem in this process according as the device is produced by the piece, consequently the production costs rise. Furthermore, there is another problem that users have the economic burden because users must buy a lot of needles which are disposables.

SUMMARY OF THE INVENTION

In the light of the foregoing, the present invention has an object to provide a set of needles for hands which are easy for mass production and economical by producing lots of needles for hands at once, and which can correctly apply acupuncture by confirming with the naked eye.

To attain the objects described above according to this invention, there is provided a set of needles for hands comprising a plurality of needles which are arranged and pressured between upper and lower synthetic resin films at regular intervals, in which cutting lines are formed between needles, having grooves and slant portions at the upper and lower parts thereof, respectively.

BRIEF DESCRIPTION OF THE DRAWINGS

The other objects and features of the present invention will be hereinafter explained in detail with reference to the accompanying drawings, wherein:

FIGS. 1(A)–1(D) show process manufacturing steps of the present invention in which:

Figure 2:
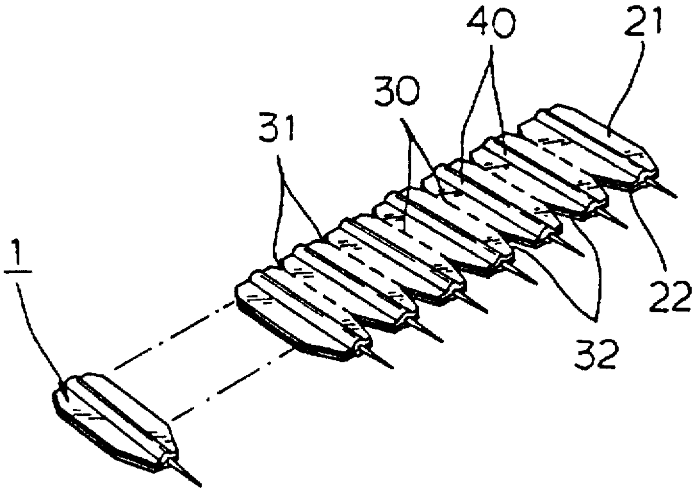
Figure 3A:
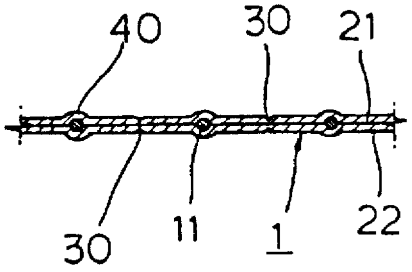
Figure 3B:
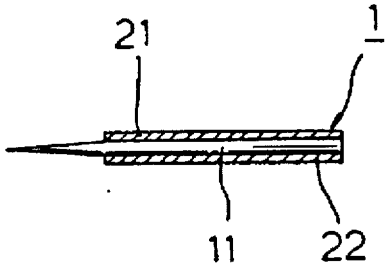

1(A) is a perspective view before a plurality of needles are pressured from between two synthetic resin films;

1(B) is a perspective view under the pressured condition;

1(C) is a perspective view with formed cutting fines in the pressured condition; and 1(D) is a perspective view showing the present invention formed grooves and slant portions;

FIG. 2 is a perspective view showing a needle for hands divided according to a cutting line; and FIGS. 3(A) and 3(B) are an enlarged cross-sectional view and an enlarged vertical-sectional view.

Figure 4:
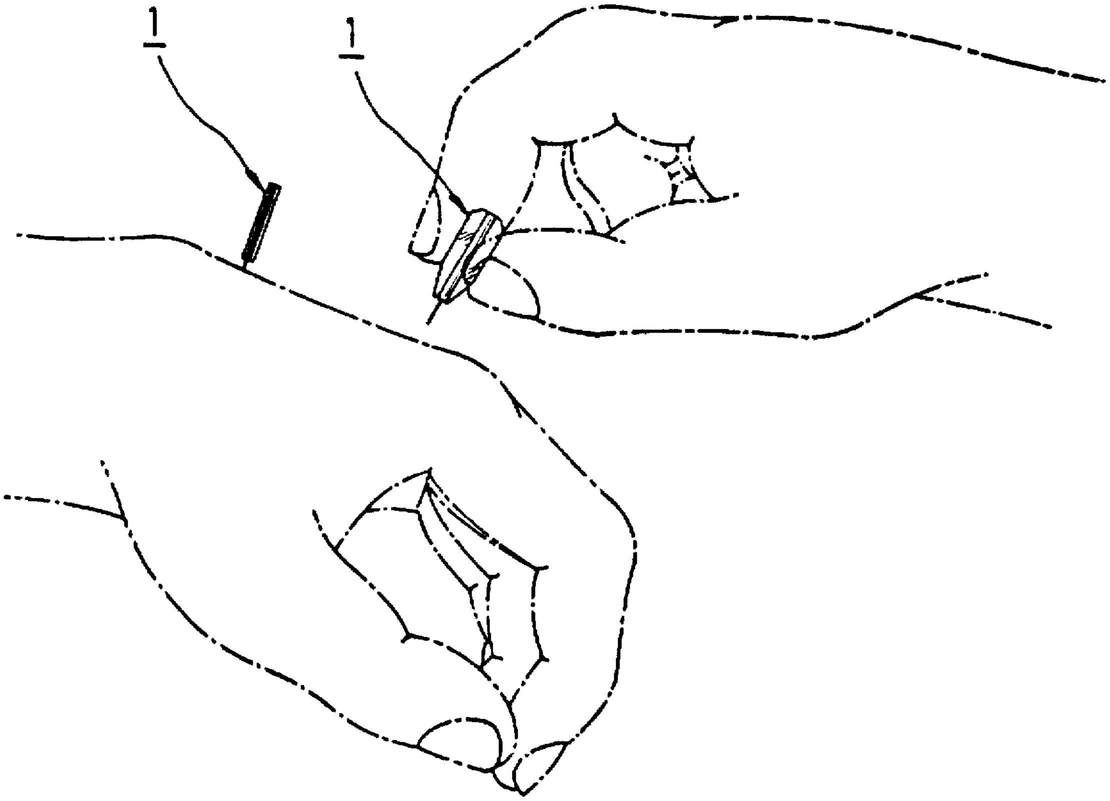

FIG. 4 is a perspective view showing the use of the needle for hands.

DESCRIPTION OF THE PREFERRED EMBODIMENT

Figure 1A:
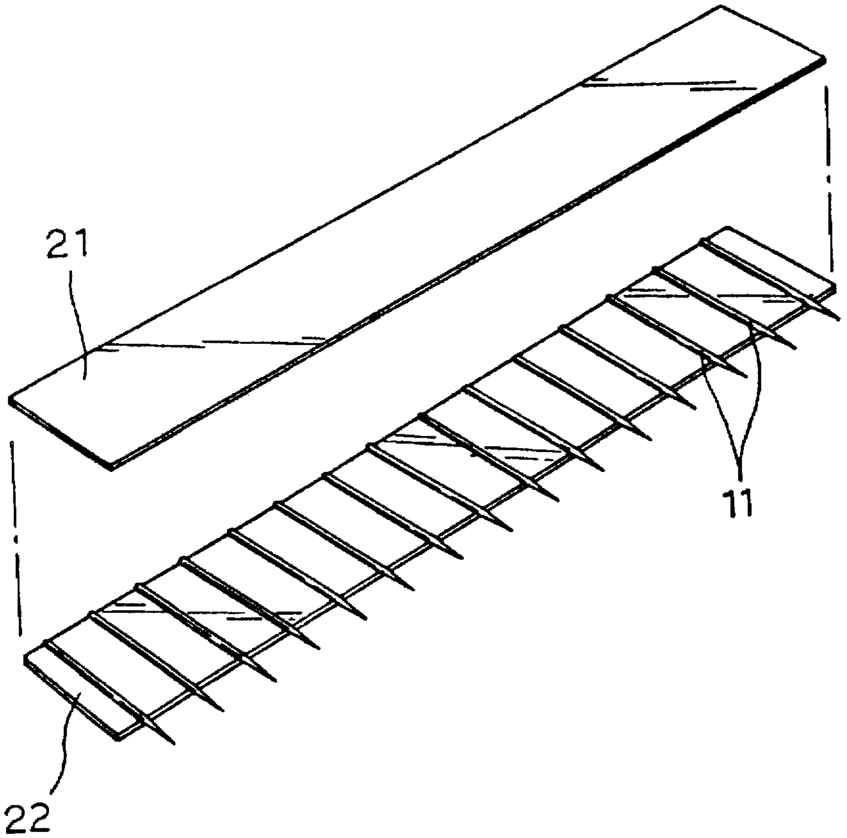
Figure 1B:
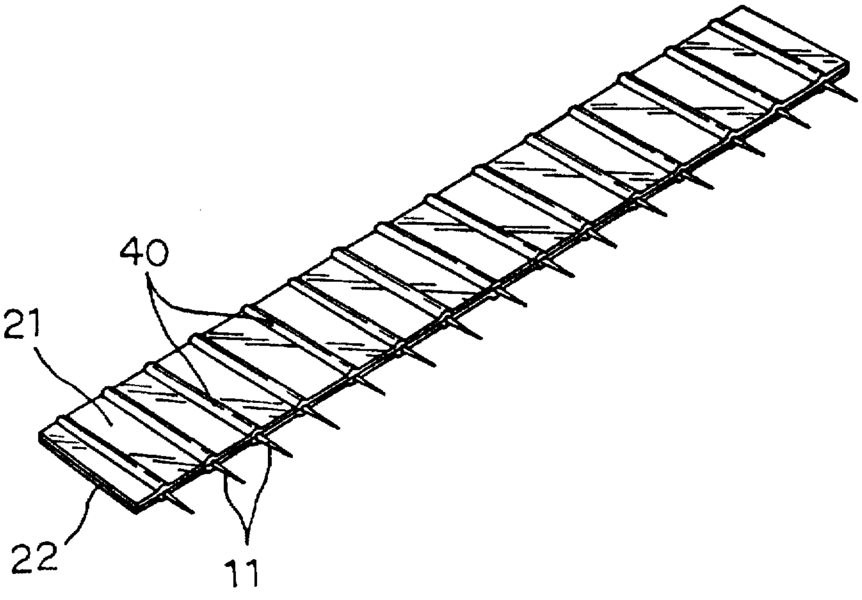
Figure 1C:
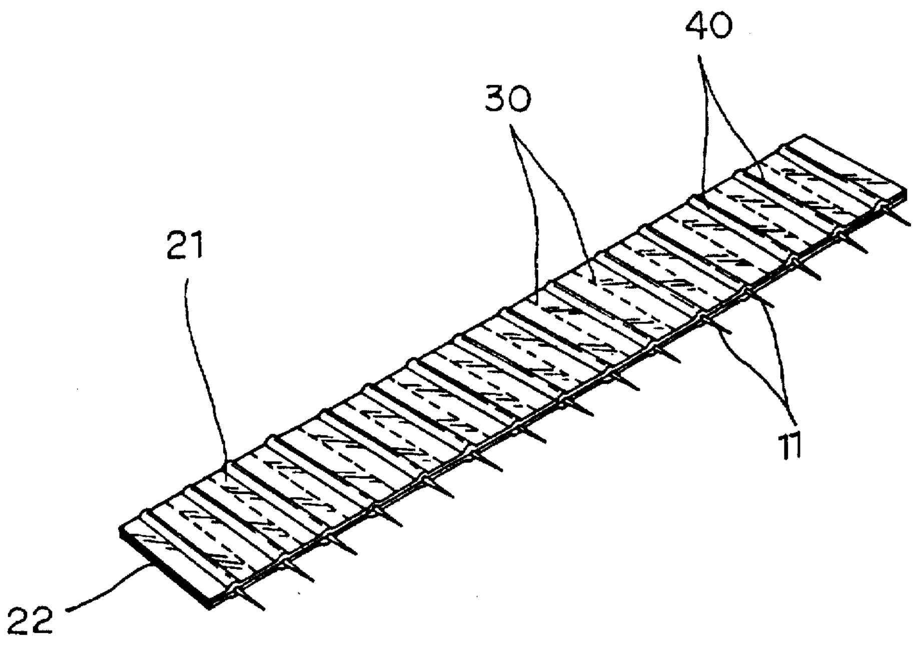
Figure 1D:
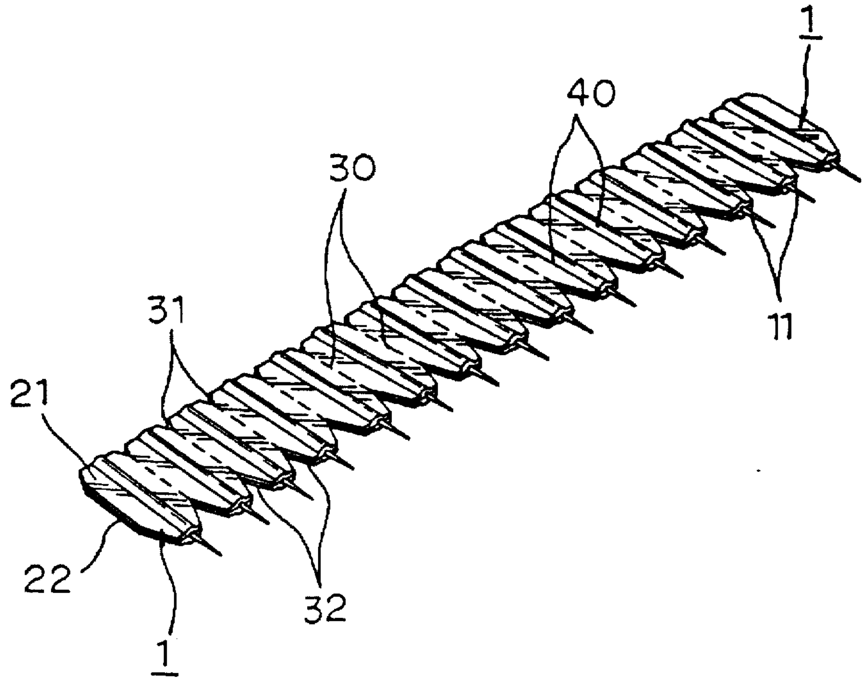

As shown the FIG. 1(A), the upper and lower synthetic resin films (21),(22) are cut in the same size, and a plurality of needles(11) are laid on the lower synthetic resin film(22) at regular intervals so that a plurality of needles (11) are projected from the bottom thereof with suitable lengths to apply acupuncture. Thereafter the upper synthetic resin film(21) is arranged in the same way. As shown the FIG. 1(B), the upper and lower synthetic resin films(21), (22) are pressured, so that the needles(11) are secured and bulging portions(40) are formed. As shown the FIG. 1(C), cutting lines(30) are formed on the upper and lower synthetic resin films(21),(22) to easily divide a needle for hands(1) from an adjacent needle for hands(1). Furthermore, as shown FIG. 1(D), grooves(31) are formed at the upper part of the cutting lines(30) to divide more easily, and slant portions(32) are formed at the lower part thereof to see whether the acupuncture is correctly applied.

To summarize the advantages obtained by the invention, as shown the FIG. 2, where necessary, each needle for hands can be used by dividing adjacent ones according to the cutting lines(30) starting from the grooves(31) which are between two needles for hands. On the other hand, because a set of needles for hands can be produced at the same time, this invention has the advantages of reduction of the manufacturing process, inexpensive supply and a reduction of the burden of household economy. When the acupuncture is applied, a user holds a holder with the bulging portion(40) and pricks needle points distributed at the skin surface of the front and back of the hand. Thus, because the user can directly prick the needle points, it is easy to control the pricking depth. Furthermore, the acupuncture is correctly applied because the user can see the needle(11) to pricked the needle points through the slant portion(32).

As mentioned above, the present invention is a useful invention that is convenient to produce, can be mass-produced, and is economical.

What is claimed is:

1. A method of using acupuncture needle assemblies for performing acupuncture treatment on hands, comprising the steps of:

providing a plurality of needles, each having a tip, sandwiched between elongated upper and lower synthetic resin films at regular intervals and such that the needles are secured between said resin films and with the tips of said needles extending out from said resin films so as to be exposed;

separating an acupuncture needle assembly, as needed, along cutting lines formed in said upper and lower synthetic resin films between said needles such that when the acupuncture needle assembly is separated along a cutting line, said needle remains secured between said separated resin films to form a separated acupuncture needle assembly; and using said separated acupuncture needle assembly to perform an acupuncture operation.

2. A method according to claim 1, wherein:

said upper and lower synthetic resin films are each formed in elongated sheets of film having a lengthwise dimension and a transverse dimension, said lengthwise dimension being much greater than said transverse dimension, each said needle extends parallel to said widthwise dimension and forms a bulging portion in each respective acupuncture needle assembly, and said plurality of needles sandwiched between elongated upper and lower synthetic resin films at regular intervals are parallel to each other.

* * * * *